United States Patent
Namba et al.

(10) Patent No.: US 10,638,758 B2
(45) Date of Patent: May 5, 2020

(54) HETEROCYCLE-CONTAINING AMINO ACID COMPOUND AND USE THEREOF

(71) Applicants: AICHI STEEL CORPORATION, Tokai-shi (JP); TOKUSHIMA UNIVERSITY, Tokushima-shi (JP)

(72) Inventors: Kosuke Namba, Tokushima (JP); Yoshiko Murata, Soraku-gun (JP)

(73) Assignees: AICHI STEEL CORPORATION, Tokai-shi (JP); TOKUSHIMA UNIVERSITY, Tokushima-shi (JP)

(*) Notice: Subject to any disclaimer, the term of this patent is extended or adjusted under 35 U.S.C. 154(b) by 41 days.

(21) Appl. No.: 15/767,660

(22) PCT Filed: Nov. 1, 2016

(86) PCT No.: PCT/JP2016/082374
§ 371 (c)(1),
(2) Date: Apr. 12, 2018

(87) PCT Pub. No.: WO2017/082111
PCT Pub. Date: May 18, 2017

(65) Prior Publication Data
US 2018/0303093 A1    Oct. 25, 2018

(30) Foreign Application Priority Data
Nov. 9, 2015    (JP) ................. 2015-219537

(51) Int. Cl.
| A01N 43/36 | (2006.01) |
| A01N 59/16 | (2006.01) |
| C05F 11/10 | (2006.01) |
| C05D 9/02 | (2006.01) |
| C07D 207/16 | (2006.01) |

(52) U.S. Cl.
CPC ............. *A01N 43/36* (2013.01); *A01N 59/16* (2013.01); *C05D 9/02* (2013.01); *C05F 11/10* (2013.01); *C07D 207/16* (2013.01); *Y02P 20/55* (2015.11)

(58) Field of Classification Search
None
See application file for complete search history.

(56) References Cited

U.S. PATENT DOCUMENTS

2010/0256395 A1    10/2010    Namba et al.

FOREIGN PATENT DOCUMENTS

| DE | 208 609 A1 | 4/1984 |
| JP | 54-128563 A | 10/1979 |
| JP | 56-63952 A | 5/1981 |
| JP | 2001-316192 A | 11/2001 |
| JP | 4117009 B2 | 7/2008 |

OTHER PUBLICATIONS

Japanese Office Action dated Jan. 9, 2018 in Patent Application No. 2017-550268 (with English translation), 7 pages.

Tsunematsu Takemoto, et al., "Structure of Mugineic Acid, a New Amino Acid Possessing an Iron-Chelating Activity from Roots Washings of Water-Cultured *Hordeum vulgare* L." Proceedings of the Japan Academy, Ser. B, vol. 54, 1978, pp. 469-473.

Ryoichi Araki, et al., "2'-Deoxymugineic Acid Promotes Growth of Rice (*Otyza sativa* L.) by Orchestrating Iron and Nitrate Uptake Processes Under High pH Conditions" The Plant Journal, vol. 81, 2015, pp. 233-246.

Hiroyuki Watanabe, "Synthesis of Mugineic Acid and Active Research" Hasegawa Letter, No. 23, 2007, pp. 34-39 (with partial English translation).

M'Barek Bouazaoui, et al., "Synthesis and Biological Activity of Nicotianamine and Analogues" Advances in Experimental Medicine and Biology, vol. 611, 2009, pp. 555-557 and cover page.

Kosuke Namba, et. al., "Mugineic Acid Derivatives as Molecular Probes for the Mechanistic Elucidation of Iron Acquisition in Barley" Angewandte Chemie International Edition, vol. 49, 2010, pp. 9956-9959.

M'Barek Bouazaoui, et al., "Efficient Synthesis of Nicotianamine and Non-Natural Analogues" European Journal Organic Chemistry, vol. 2010, Iss. 34, 2010, pp. 6609-6617.

Nicolaus Von Wiren, et al. "Nicotianamine Chelates Both $Fe^{III}$ and $Fe^{II}$. Implications for Metal Transport in Plants" Plant Physiology, vol. 119, Mar. 1999, pp. 1107-1114.

Satoshi Mori, "Iron Acquisition by Plants" Current Opinion in Plant Biology, vol. 2, 1999, pp. 250-253.

Extended European Search Report dated Mar. 25, 2019 in European Patent Application No. 16864074.6, 9 pages.

Scholz, G., et al., "Structure-Function Relationships of Nicotianamine Analogues", Phytochemistry, vol. 27 No. 9, 1988, XP026620874, pp. 2749-2754.

Suzuki, M., et al., "Novel Synthetic Analogs of Mugineic Acid Family Phytosiderophores are Effective Iron-Fertilizers in Calcareous Soils", URL: https://www.google.com/url?sa=t&rct=j&q=&esrc=s&source=web&cd=33&ved=2ahUKEwj9q5TFtiyhahUm1-AKHQA3A6U4HhAWMAJ6BAgCEAI&url=http%3A%2F%2Fcongresos.fuam.es%2Fcomunicaciones%2Fabstracts%2Fabstracts_511.doc&usg=A0vVaw2Hr-SD0aHPQmWe2RaEKz-q, 18th International Symposium on Iron Nutrition and Interaction in Plants, May 30-Jun. 3, 2016, XP055570222.

*Primary Examiner* — Alton N Pryor
(74) *Attorney, Agent, or Firm* — Oblon, McClelland, Maier & Neustadt, L.L.P.

(57) ABSTRACT

Provided is a novel heterocycle-containing amino acid compound that has a metal uptake ability equivalent to mugineic acids and can be less expensively produced than mugineic acids. Also provided are a fertilizer and a plant growth regulating agent each comprising the novel heterocycle-containing amino acid compound. The present invention is a heterocycle-containing amino acid compound represented by general formula (1):

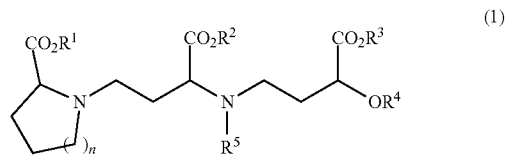

(1)

(wherein: $R^1$, $R^2$ and $R^3$ are the same or different and represent a hydrogen atom or a carboxyl-protecting group; $R^4$ represents a hydrogen atom or a hydroxy-protecting group; $R^5$ represents a hydrogen atom or an amino-protecting group; and n is an integer of 1-3) or a salt thereof and use of the same.

11 Claims, 3 Drawing Sheets

HETEROCYCLE-CONTAINING AMINO ACID COMPOUND AND USE THEREOF

TECHNICAL FIELD

The present invention relates to a novel heterocycle-containing amino acid compound and the use thereof.

RELATED ART

Various minor metal elements are involved in the growth of plants and the maintenance of their functions, and plants cannot grow normally if these minor metal elements are deficient. For example, iron is an element necessary for breathing, photosynthesis, DNA synthesis and the like, and, especially, is an active center metal of an enzyme essential for biosynthesis of chlorophyll, and thus iron deficiency causes chlorosis (iron-deficiency chlorosis) which involves yellowing of leaves.

On the other hand, defective soil which is regarded as being unsuitable for agriculture occupies about 67% of the land in the whole world, and a half thereof is alkaline defective soil. In such alkaline soil, iron is present in the form of water-insoluble trivalent ferric hydroxide (Fe(OH)$_3$), and thus plants cannot satisfactorily absorb this iron from their roots, thereby disadvantageously causing iron deficiency.

In contrast to this, it is known that graminaceous plants such as barley, rice, wheat and corn secret from their roots a chelating agent referred to as a mugineic acid represented by the following formula (A):

or as 2'-deoxymugineic acid (DMA) represented by the following formula (B):

and that the chelating agent allows formation of a complex with iron to dissolve iron so that a mugineic acid-iron complex is taken in the plant bodies via a specific transporter (see, Patent Document 1).

Thus, graminaceous plants can efficiently absorb iron ions from alkaline soil as compared with the other plants, but generally have low mugineic acid secreting ability. For example, many graminaceous plants such as rice and corn cannot grow in alkaline soil.

Accordingly, the present inventors aim at developing a chelating agent with iron uptake ability which can be supplied as a fertilizer, in order to enable agriculture even in alkaline defective soil.

The present inventors have hitherto established a practical method for synthesizing a mugineic acid (see, Non-Patent Document 1) and have confirmed a dramatic effect of this mugineic acid on the growth of graminaceous plants under alkaline conditions (see, Non-Patent Document 2).

The mugineic acid, however, is synthesized from an expensive azetidine acid as a starting raw material, and thus the supply of the mugineic acid as a fertilizer still involves a problem of the cost for synthesis thereof.

There is demanded a chelate compound which has metal uptake ability equivalent to that of mugineic acids and can be produced at a cost lower than that for mugineic acids.

PRIOR TECHNICAL DOCUMENT

Patent Document

[Patent Document 1] JP-B 4117009
[Non-Patent Document 1] Proc. Japan. Acad., Ser. B, Vol. 54, 469-473 (1978)
[Non-Patent Document 2] Plant. J., 2015, 81, pp. 233-246

SUMMARY OF THE INVENTION

Problems that the Invention is to Solve

An object of the present invention is to provide a novel heterocycle-containing amino acid compound which has metal uptake ability equivalent to that of mugineic acids and can be produced at a cost lower than that for mugineic acids.

Another object of the present invention is to provide a fertilizer or plant growth regulating agent containing such a novel heterocycle-containing amino acid compound.

Means for Solving the Problems

As a result of earnest studies in light of the aforementioned problems, the present inventors have found a novel heterocycle-containing amino acid compound which has metal uptake ability equivalent to that of the mugineic acid and can be produced at a cost lower than that for the mugineic acid. Through further studies based on such finding, the present invention has been completed.

The present invention provides the following heterocycle-containing amino acid compound and the use thereof.

(Section 1) A heterocycle-containing amino acid compound represented by a general formula (1):

wherein $R^1$, $R^2$ and $R^3$ are identical with or different from each other, and represent hydrogen atoms or carboxyl-protecting groups; $R^4$ represents a hydrogen atom or a hydroxyl-protecting group; $R^5$ represents a hydrogen atom or an amino-protecting group; and n represents an integer of 1 to 3, or a salt thereof.

(Section 2) The compound or salt thereof according to section 1, wherein the heterocycle-containing amino acid compound represented by the general formula (1) is a compound represented by a general formula (1A):

(1A)

wherein $R^1$, $R^2$, $R^3$, $R^4$, $R^5$ and n are as defined above.
(Section 3) The compound or salt thereof according to section 1 or 2, wherein $R^1$, $R^2$, $R^3$, $R^4$ and $R^5$ are each a hydrogen atom.
(Section 4) The compound or salt thereof according to any one of sections 1 to 3, wherein n is 1.
(Section 5) A complex comprising the compound or salt thereof according to any one of sections 1 to 4 and a metal.
(Section 6) The complex according to section 5, wherein the metal is iron.
(Section 7) A mixture comprising the compound or salt thereof according to any one of sections 1 to 4 and a metal compound.
(Section 8) The mixture according to section 7, wherein the metal compound is an iron compound.
(Section 9) The mixture according to section 7 or 8, which is used for a fertilizer or a plant growth regulating agent.
(Section 10) A fertilizer comprising the compound or salt thereof according to any one of sections 1 to 4, the metal complex according to section 5 or 6, or the mixture according to any one of sections 7 to 9.
(Section 11) A plant growth regulating agent comprising the compound or salt thereof according to any one of sections 1 to 4, the metal complex according to section 5 or 6, or the mixture according to any one of sections 7 to 9.

Effect of the Invention

The novel heterocycle-containing amino acid compound or a salt thereof in the present invention has metal uptake ability equivalent to that of mugineic acids and can be produced at a cost lower than that for mugineic acids.

The novel heterocycle-containing amino acid compound or a salt thereof in the present invention can be used as a fertilizer and a plant growth regulating agent, and exerts a great effect on the growth of plants (such as graminaceous plants) also in alkaline soil.

EMBODIMENTS FOR CARRYING OUT THE INVENTION

The heterocycle-containing amino acid compound represented by the general formula (1) or a salt thereof according to the present invention (hereinafter, referred to as "heterocycle-containing amino acid compound (1) of the present invention" or "compound (1) of the present invention"), and the intended use thereof will be described in detail below.

In the specification, the expression "contain" or "comprise," as used herein, includes the concepts of "contain," "comprise," "consist substantially of" and "consist only of."

Heterocycle-Containing Amino Acid Compound (1)

In the specification, the "carboxyl-protecting group" represented by $R^1$, $R^2$ and $R^3$ is not particularly limited and example thereof includes $C_{1-6}$ linear, branched or cyclic alkyl groups, such as methyl group, ethyl group, n-propyl group, iso-propyl group, n-butyl group, iso-butyl group, tert-butyl group, n-hexyl group, and cyclohexyl group; aralkyl groups which may have a substituent, such as benzyl group, p-nitrobenzyl group, o-nitrobenzyl group, m-nitrobenzyl group, 2,4-dinitrobenzyl group, p-chlorobenzyl group, p-bromobenzyl group, and p-methoxybenzyl group; $C_{1-6}$ alkylcarbonyloxy-$C_{1-6}$ alkyl groups, such as acetoxymethyl group, acetoxyethyl group, propionyloxymethyl group, n-butyryloxymethyl group, iso-butyryloxymethyl group, and pivaloyloxymethyl group; and the like.

Among others, the carboxyl-protecting group is preferably a $C_{1-6}$ alkyl group, more preferably an ethyl group or tert-butyl group, and particularly preferably an ethyl group.

In the specification, "n-" means normal; "iso-" means iso; "tert-" or "t-" means tertiary; "o-" means ortho; "m-" means meta; and "p-" means para.

In the specification, the "hydroxyl-protecting group" represented by $R^4$ is not particularly limited, and example thereof includes $C_{1-6}$ linear or branched alkyl groups, such as methyl group, ethyl group, n-propyl group, iso-propyl group, n-butyl group, iso-butyl group, tert-butyl group, and n-hexyl group; aralkyl groups which may have 1 to 5 substituents, such as benzyl group, p-nitrobenzyl group, o-nitrobenzyl group, m-nitrobenzyl group, 2,4-dinitrobenzyl group, p-chlorobenzyl group, p-bromobenzyl group, and p-methoxybenzyl group; trialkylsilyl groups such as trimethylsilyl group, triethyleilyl group, and tert-butyldimethyl silyl group; acetal-type protecting groups such as tetrahydropyran-2-yl group, methoxymethyl group, and methoxyethoxymethyl group; alkoxycarbonyl groups such as tert-butoxycarbonyl group; and the like.

Among others, the hydroxyl-protecting group is preferably a $C_{1-6}$ alkyl group, more preferably an ethyl group or tert-butyl group, and particularly preferably a tert-butyl group.

In the specification, examples of the "amino-protecting group" represented by $R^5$ include alkoxycarbonyl groups which may be substituted by halogen, such as methoxycarbonyl group, ethoxycarbonyl group, 2,2,2-trichloroethoxycarbonyl group, and tert-butoxycarbonyl group (BOC); alkenyloxycarbonyl groups such as vinyloxycarbonyl group; aralkyloxycarbonyl groups such as benzyloxycarbonyl group (Cbz) and 9-fluorenylmethoxycarbonyl group; aralkyl groups which may have a substituent, such as benzyl group, p-nitrobenzyl group, o-nitrobenzyl group, m-nitrobenzyl group, 2,4-dinitrobenzyl group, p-chlorobenzyl group, p-bromobenzyl group, and p-methoxybenzyl group; acyl groups such as formyl group, acetyl group, trifluoroacetyl group, and benzoyl group; arylsulfonyl groups such as p-toluenesulfonyl group and benzenesulfonyl group; alkylsulfonyl groups such as methanesulfonyl group; and the like.

Among these, the amino-protecting group is preferably an alkoxycarbonyl group or an aralkyloxycarbonyl group, and more preferably a Boc or Cbz.

The symbol "n" is an integer of 1 to 3. Specifically, the compound where n is 1, 2 or 3 is the following compound (1-1), (1-2) or (1-3).

The compound is preferably one wherein n is 1 or 2, and more preferably one wherein n is 1.

Salts of the heterocycle-containing amino acid compound represented by the general formula (1) include any kinds of salts so long as they are agriculturally acceptable. Examples of such salts include inorganic acid salts such as hydrochloride, sulfate and nitrate; organic acid salts such as acetate and methanesulfonate; alkali metal salts such as sodium salt and potassium salt; alkali earth metal salts such as magnesium salt and calcium salt; and quaternary ammonium salts such as dimethyl ammonium and triethyl ammonium; and the like.

Among the heterocycle-containing amino acid compounds (1) of the present invention, a preferable compound is a compound in which $R^1$, $R^2$ and $R^3$ are identical with or different from each other, and represent hydrogen atoms or linear or branched $C_{1-6}$ alkyl groups; $R^4$ is a hydrogen atom or a linear or branched $C_{1-6}$ alkyl group; and $R^5$ is a hydrogen atom or a linear or branched $C_{1-6}$ alkyl group, or a salt thereof.

A more preferable compound is a compound in which $R^1$, $R^2$ and $R^3$ are identical with or different from each other, and represent hydrogen atoms, ethyl groups or t-butyl groups; $R^4$ is a hydrogen atom or tert-butyl group; and $R^5$ is a hydrogen atom, or a salt thereof.

A furthermore preferable compound is compound in which $R^1$ and $R^2$ are identical with or different from each other, and represent hydrogen atoms or ethyl groups; $R^3$ is a hydrogen atom or tert-butyl group; $R^4$ is a hydrogen atom or tert-butyl group; and $R^5$ is a hydrogen atom, or a salt thereof.

A particularly preferable compound is a compound in which $R^1$, $R^2$, $R^3$, $R^4$ and $R^5$ are each a hydrogen atom, or a salt thereof.

It is noted that a compound in which $R^1$, $R^2$, $R^3$, $R^4$ and $R^5$ are each a hydrogen atom, represented by the formula (1B-1):

wherein n is an integer of 1 to 3
can also be indicated by a compound represented by the following compound (1B-2):

wherein n represents an integer of 1 to 3.

When the compound (1) of the present invention has isomers such as optical isomers, stereoisomers or position isomers, either one of the isomers and mixtures of the isomers are also included in the compound (1). When optical isomers are present in the compound (1) of the present invention, optical isomers divided from a racemic body are also included in the compound (1). These isomers can each be obtained as a single product by known synthesis method and separation method (such as concentration, solvent extraction, column chromatography and recrystallization).

Optical isomers which are preferable as the compound (1) of the present invention are compounds of the general formula (1A):

wherein $R^1$, $R^2$, $R^3$, $R^4$, $R^5$ and n are as defined above, or salts thereof.

As the compounds represented by the general formula (1A), compounds in which $R^1$, $R^2$, $R^3$, $R^4$ and $R^5$ are each a hydrogen atom, and n is 1 or 2 (more preferable 1) are preferable.

Complex Containing the Heterocycle-Containing Amino Acid Compound (1) of the Present Invention and Metal The heterocycle-containing amino acid compound (1) of the present invention can form a complex with a metal. A complex containing the heterocycle-containing amino acid compound (1) of the present invention and a metal (hereinafter referred to as "complex of the present invention" in some cases) can be produced, for example, by dissolving the heterocycle-containing amino acid compound (1) of the present invention and a metal compound which will be described below in an appropriate solvent such as water and buffer.

The heterocycle-containing amino acid compound (1) of the present invention is identical with the compound (1) described above.

The metal is not particularly limited so long as it is necessary in plant bodies, and examples thereof include major elements such as magnesium (magnesia, Mg) and calcium (Ca); and minor elements such as iron (Fe), manganese (Mn), zinc (Zn), molybdenum (Mo) and copper (Cu). Among these, the metal is preferably a copper or iron, and more preferably a iron. These metals are usually present in the state of metal ions (metal ions such as monovalent, divalent and trivalent metal ions), but sometimes form a complex in the state of zero-valent metals. The metal may be contained singly or in combination of two or more types thereof.

A content of the metal is not particularly limited and can appropriately be selected depending on the purpose. Among others, the content of the metal is usually in a range from 0.1% to 100% by mol, and preferably 100% by mol relative to the compound (1).

Mixture Containing the Heterocycle-Containing Amino Acid Compound (1) of the Present Invention and Metal The heterocycle-containing amino acid compound of the present invention can lead mixture by further containing a metal compound. The mixture (hereinafter, referred to as "mixture of the present invention" in some cases) containing the heterocycle-containing amino acid compound (1) of the present invention and a metal can be produced merely by mixing a solid compound (1) of the present invention and a solid metal compound.

The heterocycle-containing amino acid compound (1) of the present invention is identical with the compound (1) described above.

The metal compound to be mixed is not particularly limited so long as it has a metal that is necessary in plant bodies, and example thereof includes magnesium compounds, calcium compounds, iron compounds, manganese compounds, boron compounds, zinc compounds, molybdenum compounds, copper compounds, and the like.

Examples of the magnesium compounds include magnesium hydroxide, magnesium chloride, and the like.

Examples of the calcium compounds include calcium hydroxide, calcium carbonate, calcium chloride, and the like.

Examples of the iron compounds include iron sulfate, iron nitrate, iron oxide ($Fe_2O_3$), ferric chloride ($FeCl_3$) or hydrates thereof, and the like.

Examples of the manganese compounds include manganese dioxide, manganese sulfate pentahydrates, manganese chloride tetrahydrates, and the like.

Examples of the boron compounds include sodium tetraborate decahydrates, boric acid, and the like.

Examples of the zinc compounds include zinc sulfate, zinc bodies, and the like.

Examples of the molybdenum compounds include sodium molybdate, ammonium molybdate, and the like.

Examples of the copper compounds include copper sulfate, copper, and the like.

Among these, the metal compound is preferably copper compounds or iron compounds, more preferably ferric chloride, and particularly preferably a ferric chloride hexahydrate.

The metal compound may be contained singly or in combination of two or more types thereof.

A content of the metal compound is not particularly limited and can appropriately be selected depending on the purpose. The content of the metal compound is usually in a range from 0.1% to 100% by mol, and preferably 100% by mol relative to the compound (1).

Production Method of Heterocycle-Containing Amino Acid Compound (1) of the Present Invention A method for producing the heterocycle-containing amino acid compound (1) of the present invention includes the following steps 1 to 4.

wherein $R^{10}$, $R^{20}$ and $R^{30}$ are identical with or different from each other, and represent carboxyl-protecting groups; $R^{40}$ represents a hydroxyl-protecting group; $R^{50}$ represents an amino-protecting group; and $R^5$ is as defined above.

The carboxyl-protecting groups, hydroxyl-protecting group and amino-protecting group indicated in this formula have the same meanings as the respective protecting groups represented by $R^1$, $R^2$, $R^3$, $R^4$ and $R^5$ described above.

Hereinafter, respective steps are described.

(1) Step 1

Step 1 is a process for oxidatively cleaving a vinyl group of a compound represented by the general formula (5) (hereinafter, referred to as compound (5)) to form an aldehyde, and reacting the aldehyde with a compound represented by the general formula (6) (hereinafter, referred to as compound (6)) (reductive amination reaction), thereby yielding a compound represented by the general formula (4) (hereinafter, referred to as compound (4)).

The compound (5) is allyl glycine whose amino group is protected by a protecting group ($R^{50}$) and examples thereof include Boc-L-allyl glycine, Cbz-L-allyl glycine, and a compound whose carboxyl group is protected by a protecting group.

A commercial product can be used as the compound (5), or, if there is no commercial product, Boc-L-allyl glycine and Cbz-L-allyl glycine can be produced from commercial L-allyl glycine in accordance with the method described in PROTECTIVE GROUPS in ORGANIC SYNTHESIS (authored by T. W. Green; P. G. M. Wuts).

Examples of the compound (6) include proline, pipecolic acid, azepine-2α-carboxylic acid, and the like.

Step 1 includes a step of oxidatively cleaving a vinyl group of the compound (5) to yield an aldehyde, and a step of subjecting the aldehyde to reductive amination reaction with the compound (6).

The proportions of the compounds (5) and (6) to be used are particularly limited and can appropriately be selected from a wide range. Usually, the compound (6) is used in an amount of about 1 to 5 mol, and preferably about 1 to 2 mol relative to 1 mol of the compound (5).

The reaction for the oxidative cleavage step is conducted in the presence of an oxidant. Examples of the oxidant include ozone ($O_3$), permanganates, $RuCl_3$, $OsO_4$—$NaIO_4$, and the like. The oxidant is preferably an ozone.

The amount of the oxidant to be used is not particularly limited.

The oxidative cleavage reaction using ozone can be carried out by blowing ozone gas into a solution obtained by dissolving the compound (5) in a solvent (bubbling).

Examples of the solvent include an organic solvent such as alcohol-based solvents including methanol and ethanol; chlorine-based solvents including dichloromethane, and chloroform; and ethyl acetate. The solvent is preferably a methanol.

The reaction temperature for the oxidative cleavage step is not particularly limited, and the bubbling of ozone gas is preferably conducted at a low temperature ranging from about −100 to −50° C.

The reaction time for the oxidative cleavage step is not particularly limited, and the bubbling of ozone gas is preferably conducted until the color of the solution turns blue since the solution is colored blue when ozone is saturated in the solution after completion of oxidative cleavage by ozone.

The ozone gas can be generated by means of an ozone gas generator or the like. After the bubbling of the ozone gas, oxygen, nitrogen, argon gas or the like is preferably bubbled into the solution until the blue color of the solution disappears, in order to remove excessive ozone. Thus, an aldehyde is obtained.

Next, the reductive amination reaction between the aldehyde and the compound (4) is conducted in the presence of a reducing agent. Following the oxidative cleavage reaction, the reductive amination reaction can be carried out in one pot. Alternatively, the reaction can be carried out in another reaction system after the obtainment of an aldehyde after the oxidative cleavage reaction.

Examples of the reducing agent include boron compounds such as sodium cyanoborohydride and sodium triacetoxyborohydride. The reducing agent is preferably a sodium cyanoborohydride.

An amount of the reducing agent to be used is not particularly limited, and can appropriately be selected from a wide range. The reducing agent is usually used in an amount of about 1 to 5 mol and preferably about 1 to 2 mol relative to 1 mol of the compound (5).

A pH used in the reductive amination reaction is usually about 4 to 7, and preferably about 6 to 7.

The reaction temperature for the reductive amination reaction is not particularly limited, and generally, the reaction may be conducted under any of cooling, room temperature and heating. The reaction is preferably conducted under a temperature condition of about 25° C. to 50° C. for 30 minutes to 24 hours.

The compound (4) obtained in the step 1 can be isolated and purified from the reaction mixture, by separating a coarse reaction product through an isolating operation such as filtration, concentration or extraction, after cooling of the reaction mixture, and carrying out an ordinary purifying operation such as column chromatography, ion exchange resins or recrystallization. The compound (4) can also be used for a next reaction without being isolated or purified.

(2) Step 2

Step 2 is a process for protecting the carboxyl groups of the compound (4) by protecting groups ($R^{10}$ and $R^{20}$) and deprotecting the protecting group ($R^{50}$) of the amino group, thereby yielding a compound represented by the general formula (3) (hereinafter, referred to as "compound (3)") or a salt thereof.

The reaction for protecting the carboxyl groups with protecting groups ($R^{10}$ and $R^{20}$) is not particularly limited, and publicly known methods can be used. For example, a method including dehydration condensation reaction between the compound (4) and an alcohol is used. Examples of the alcohol used for the reaction include methanol, ethanol, tert-butanol, and the like.

The reaction for deprotecting the protecting group ($R^{50}$) of the amino group is not particularly limited, and a deprotecting method using an acid or base, a deprotecting method through catalytic reduction or the like can be employed in accordance with the known method described in the document (see, Protective Groups in Organic Synthesis, T. W. Greene, John Wiley & Sons (1981)).

Examples of the acid include inorganic acids such as hydrogen chloride (or hydrochloric acid), hydrogen bromide (or hydrobromic acid), hydrogen fluoride (or hydrofluoric acid), hydrogen iodide (or hydroiodic acid), trifluoroacetic acid, aluminum chloride, aluminum bromide, boron trichloride, boron tribromide, sulfuric acid and phosphoric acid; organic acids such as formic acid, acetic acid, trifluoroacetic acid, propionic acid, methanesulfonic acid, p-toluenesulfonic acid and trifluoromethanesulfonic acid; acidic ion exchange resins; and the like.

Examples of the base include inorganic bases such as sodium hydroxide, potassium hydroxide, calcium hydroxide and magnesium hydroxide; organic bases such as metal alkoxides, organic amines and quaternary ammonium salts; basic ion exchange resins; and the like.

An amount of the acid or base to be used is usually in a range from 1 to 50 mol, and preferably from 1 to 30 mol relative to 1 mol of the compound (4).

The deprotecting reaction using an acid or base can be conducted in a solvent-free manner or in a solvent. When a solvent is used, the solvent is not particularly limited so long as it does not adversely affect the reaction. Examples of the solvent include an alcohol-based solvent such as methanol and ethanol; an aprotic polar solvent such as acetonitrile, DMF and DMSO; a halogenated hydrocarbon-based solvent such as DCM and DCE; or a solvent mixture thereof.

When $R^{50}$ of the compound (4) is a Boc group or the like, the reaction for protecting the carboxyl groups by protecting groups and the reaction for deprotecting the protecting group ($R^{50}$) of the amino group can be conducted simultaneously by reacting the compound (4) and a hydrochloric acid/ethanol solution. The hydrochloric acid/ethanol solution can be prepared, for example, by a method of adding acetyl chloride (AcCl) to an excessive amount of ethanol or a method of bubbling hydrochloric acid gas into ethanol.

A proportion of ethanol to acetyl chloride is not particularly limited and is about 20 to 50 times volume relative to 1 volume of acetyl chloride.

When hydrochloric acid gas is bubbled into ethanol, the amount of dissolved hydrochloric acid t can be determined by comparing the preliminarily measured weight of ethanol and the weight of ethanol after bubbling of hydrochloric acid gas. After completion of the reaction in the step 2, the reaction mixture is concentrated under a reduced pressure; then toluene or the like is added thereto; and the resultant mixture is subjected to azeotropic distillation, thereby making it possible to distill away the solvent. Further, after azeotropic distillation, the reaction product can be sucked by a vacuum pump or the like to be dried.

The reaction temperature used for the step 2 is not particularly limited, and the reaction may be conducted under any of cooling, room temperature and heating. The reaction is preferably conducted under a temperature condition of about 0 to 100° C. for 1 to 30 hours.

The deprotecting method through catalytic reduction can be applied to the case where $R^{50}$ of the compound (4) is a group to be hydrocracked. For example, a method to be conducted through hydrocracking by a transition metal catalyst such as Pd, Pt, Ru or Rh; a method to be carried out through hydrocracking by a catalyst having carried thereon a transition metal such as Pd-carbon, palladium hydroxide-carbon (Pearlman's catalyst) or the like; and a Birch reducing method can be applied. Among others, a preferable transition metal catalyst is Pd-carbon.

An amount of the transition metal catalyst to be used is usually in a range from 0.01 to 5 mol, and preferably from 0.05 to 2 mol relative to 1 mol of the compound (4).

The reaction through catalytic reduction is conducted in a hydrogen atmosphere at a pressure of usually 1 to 4 atm, and preferably 1 to 2 atm.

The reaction is usually carried out in a solvent. The solvent is not particularly limited so long as it is not involved in the reaction. Examples of the solvent include an alcohol-based solvent such as methanol and ethanol; an ether-based solvent such as THF, MTBE, dioxane, diethyl ether, dimethoxyethane, and diglyme; an ester-based solvent such as methyl acetate and ethyl acetate; a halogenated hydrocarbon-based solvent such as DCM and DCE; water; or a solvent mixture thereof. An alcohol-based solvent such as methanol and ethanol is preferably used.

The reaction temperature for the deprotecting method through catalytic reduction is not particularly limited, and the reaction may be conducted under any of cooling, room temperature and heating. The reaction is preferably conducted under a temperature condition of about room temperature to 40° C. for 1 to 24 hours.

The compound (3) obtained in the step 2 can be isolated and purified from the reaction mixture, by separating a coarse reaction product through an isolating operation such as filtration, concentration or extraction, after cooling of the reaction mixture, and carrying out an ordinary purifying operation such as column chromatography, ion exchange resins or recrystallization. The compound (3) can also be used for a next reaction without being isolated or purified.

While the obtained compound (3) has a free amino group, the amino group can be converted into a salt of an acid such as hydrochloric acid or sulfuric acid using a known method.

(3) Step 3

Step 3 is a process for causing reductive amination reaction between the compound (3) and an aldehyde compound represented by the general formula (2) (hereinafter, referred to as "aldehyde compound (2)"), thereby yielding a compound represented by the general formula (1') (hereinafter, referred to as "compound (1')").

The reaction in the step 3 can usually be conducted in the presence of a reducing agent which is used in the reductive amination reaction described for the step 1 above, in a solvent.

An amount of the reducing agent to be used is usually in a range from 0.5 to 10 mol, and preferably from 1 to 6 mol relative to 1 mol of the compound (3).

The aldehyde compound (2) can be easily produced in accordance with, for example, the method described in Nishimaru, T. et al. Peptide Science 2006, 42, 263-266.

An amount of the aldehyde compound (2) to be used is usually at least 1 mol, preferably about 1 to 5 mol relative to 1 mol of the compound (3).

Any solvent may be used so long as it does not adversely affect the reaction. Examples of the solvent include an alcohol-based solvent such as methanol, ethanol, isopropanol, and ethyleneglycol; an aprotic polar solvent such as acetonitrile, DMF, and dimethylsulfoxide; or a solvent mixture thereof.

The reaction temperature is not particularly limited, and generally, the reaction may be conducted under any of cooling, room temperature and heating. The reaction is preferably conducted under a temperature condition of about 0 to 100° C. for 1 to 30 hours.

Further, the secondary amino group of the compound obtained by the reductive amination reaction may be protected by an amino-protecting group ($R^{50}$) using a known method.

The compound (1') obtained in the step 3 can be isolated and purified from the reaction mixture, by separating a coarse reaction product through an isolating operation such as filtration, concentration or extraction, after cooling of the reaction mixture, and carrying out an ordinary purifying operation such as column chromatography, ion exchange resins or recrystallization. The compound (1') can also be used for a next reaction without being isolated or purified.

(4) Step 4

Step 4 is a process for deprotecting the carboxyl-protecting groups ($R^{10}$, $R^{20}$ and $R^{30}$), hydroxyl-protecting group ($R^{40}$) and, as necessary, amino-protecting group ($R^{50}$) in the compound (1'), thereby yielding a compound represented by the general formula (1B-1) (hereinafter, referred to as "compound (1B-1)").

Examples of the deprotecting method in the step 4 include the deprotecting method using an acid or base and deprotecting method through catalytic reduction as described for the step 2 above and a combination thereof. Known methods can be used as all of these deprotecting methods.

When all of the protecting groups $R^{10}$, $R^{20}$, $R^{30}$, $R^{40}$ and $R^5$ are protecting groups which can be deprotected by an acid, a deprotecting method using an acid can be used. When all of the protecting groups $R^{10}$, $R^{20}$, $R^{30}$, $R^{40}$ and $R^5$ are protecting groups which can be deprotected by a base, a deprotecting method using a base can be used. When all of the protecting groups $R^{10}$, $R^{20}$, $R^{30}$, $R^{40}$ and $R^5$ include both of protecting groups which can be deprotected by a base and protecting groups which can be deprotected by an acid, a deprotecting method using an acid and a deprotecting method using a base can be carried out in combination.

Specifically, when the protecting groups $R^{10}$ and $R^{20}$ are ethyl groups, $R^{30}$ and $R^{40}$ are t-butyl groups, and $R^5$ is a hydrogen atom (see Example 2), the treatment with an acid and the treatment with a base can be used in combination for deprotection. Examples of the acid include trifluoroacetic acid, and examples of the base include sodium hydroxide (1N aqueous sodium hydroxide solution). The order of acid treatment and base treatment is not particularly limited, and either a method comprising base treatment followed by acid treatment or a method comprising acid treatment followed by base treatment may be used.

The deprotecting method using an acid or base can usually be conducted in a solvent. Examples of the solvent include water; an alcohol-based solvent such as methanol, ethanol and t-butanol; a halogenated hydrocarbon-based solvent such as methylene chloride (DCM), chloroform, and 1,2-dichloroethane (DCE); an ether-based solvent such as tetrahydrofuran (THF), methyl-t-butylether (MTBE), dioxane, diethylether, dimethoxyethane, and diglyme; ethyl acetate; a ketone-based solvent such as acetone and methylethylketone; acetic acid; or solvent mixtures thereof.

An amount of the acid or base to be used is not particularly limited and is usually in a range from 1 to 20 mol, and preferably from 1 to 10 mol relative to 1 mol of the compound (1').

In the deprotecting method using an acid or base, when the acid or base itself is a liquid, it can also play a role of solvent. Therefore, the acid or base can be added in an excessive amount.

The reaction temperature is not particularly limited, but the reaction may be usually conducted under any of cooling, room temperature and heating. The reaction is preferably conducted under a temperature condition of around room temperature to about 85° C. for 30 minutes to 30 hours.

The compound (1B-1) obtained in the step 4 can be isolated and purified from the reaction mixture, by separating a coarse reaction product through an isolating operation such as filtration, concentration or extraction, after cooling of the reaction mixture, and carrying out an ordinary purifying operation such as column chromatography, ion exchange resins or recrystallization.

The heterocycle-containing amino acid compound (1) of the present invention is a concept encompassing the aforementioned compound (1') and compound (1B-1).

Applications

The heterocycle-containing amino acid compound (1) of the present invention, the complex of the present invention and the mixture of the present invention as described above can be used in applications such as a fertilizer, and a plant growth regulating agent.

The term "plant growth regulating agent" means either one of a plant growth suppressor (plant growth inhibitor) or a plant growth promoter. In the specification, the "plant growth regulating agent" as used herein includes the meaning of "hormone."

The heterocycle-containing amino acid compound (1) in the fertilizer or plant growth regulating agent of the present invention may be contained singly or in combination of two or more types thereof.

The fertilizer or plant growth regulating agent of the present invention can include known fertilizers, known plant growth regulating agents, known plant hormones and the like in addition to the heterocycle-containing amino acid compound (1) of the present invention, the complex of the present invention or the mixture of the present invention as described above.

The fertilizer or plant growth regulating agent of the present invention is preferably a solid such as powder from the viewpoint of the convenience of distribution, storage and the like and the storage stability. During use, the fertilizer or plant growth regulating agent is preferably used in a form suitable for a cultivation method. In conventional soil culture methods, powder can be applied, as it is, to soil. In hydroponic soil culture methods, powder can be dissolved in water to be used in an aqueous solution form.

In the present invention, crops encompass all agricultural and horticultural plants which have been conventionally cultivated, and specific examples thereof can include graminaceous plants such as rice, wheat and corn; vegetables; fruits; flowering plants; and foliage plants.

EXAMPLES

The heterocycle-containing amino acid compound of the present invention and the method for producing the compound will be described in detail by showing Examples and Comparative Examples. The present invention is not limited to the Examples.

The following abbreviations are used in some cases in the Examples and Comparative Examples.
Et: ethyl group
Bu: butyl group
MeOH: methanol
EtOH: ethanol
NaBH$_3$CN: sodium cyanoborohydride
TLC: thin layer chromatography
CHCl$_3$: chloroform
TFA: trifluoroacetic acid
NH$_3$: ammonia
Boc: tert-butoxycarbonyl group
M: molar concentration, mol/L Reference Example 1: Production of Compound (4a-1)

A methanol solution of Boc-L-allyl glycine (5a-1) (197 mg, 0.91 mmol) was cooled to −78° C., and ozone gas (O$_3$) was bubbled thereto until the solution turned blue. N$_2$ was bubbled until the blue color disappeared, and thereafter L-proline (6a-1) (116 mg, 1.0 mmol) and NaBH$_3$CN (62.8 mmol, 1.0 mmol) were added to this solution, and the solution was stirred at room temperature for 1 hour. The completion of the reaction was confirmed by TLC, and thereafter this solution was concentrated under a reduced pressure. The obtained residue was purified by flash column chromatography (CHCl$_3$: MeOH=2:1→1:1), thereby yielding a colorless oily compound (4a-1) (326.2 mg, 0.91 mmol).

Compound (4a-1):

$^1$H NMR (400 MHz, CD$_3$OD): d=4.08 (t, J=5.6 Hz, 1H), 3.86 (dd, J=9.2, 5.6 Hz, 1H), 3.73 (ddd, J=10.8, 7.2, 4.0 Hz, 1H), 3.48-3.38 (m, 1H), 3.18-3.05 (m, 2H), 2.47-2.37 (m, 1H), 2.25-2.03 (m, 4H), 2.00-1.88 (m, 1H), 1.44 (s, 9H)

Example 1: Production of Compound (1a-1)

Cooled anhydrous HC/EtOH (HCl/EtOH prepared from acetyl chloride (2 mL) and ethanol (25 mL)) was added to the compound (4a-1) (326.2 mg, 0.91 mmol), and the solution was stirred at room temperature for 21 hours. The completion of the reaction was confirmed by TLC, and thereafter this solution was concentrated under a reduced pressure. The obtained residue was dehydrated by toluene azeotropy, and dried in vacuo for several hours. An aldehyde compound (2a-1) (635 mg, 2.76 mmol) and NaBH$_3$CN (180 mg, 2.86 mmol) were added to a methanol (15 mL) solution of the obtained residue, and the solution was stirred at room temperature for 10 hours. The completion of the reaction was confirmed by TLC, and thereafter a saturated aqueous sodium hydrogen carbonate solution (30 mL) was added to this reaction solution. This solution was extracted with ethyl acetate, and the collected organic layer was dried with magnesium sulfate. Thereafter, filtration was conducted, and the filtrate was concentrated under a reduced pressure. The obtained residue was purified by flash column chromatography (n-hexane/ethyl acetate (2:1)→ethyl acetate), thereby yielding a colorless oily compound (1a-1) (38.6 mg, 0.079 mmol, 9%).

Compound (1a-1):

$^1$H NMR (400 MHz, CD$_3$OD): d=4.17 (dq, J=10.4, 3.2 Hz, 4H), 4.02 (dd, J=6.8, 4.8 Hz, 1H), 3.35 (t, J=6.8 Hz, 1H), 3.20-3.11 (m, 2H), 2.83-2.76 (m, 1H), 2.72-2.65 (m, 1H), 2.60-2.47 (m, 2H), 2.37 (dd, J=16.4, 8.4 Hz, 1H), 2.13 (m, 1H), 1.93-1.74 (m, 7H), 1.47 (s, 9H), 1.27 (dt, J=7.6, 4.4 Hz, 6H), 1.18 (s, 9H)

Example 2: Production of Compound (1b-1)

TFA (0.3 mL) was added to a CH$_2$Cl$_2$ (0.6 mL) solution of the compound (1a-1) (38.6 mg, 0.079 mmol), and the solution was stirred at room temperature for 18 hours. The completion of the reaction was confirmed by TLC, and thereafter this solution was concentrated under a reduced pressure. To the obtained residue, 1 M aqueous sodium hydroxide solution (0.42 mL) was added, and was stirred at 0° C. for 3 hours. Thereafter, the temperature of the reaction solution was increased to room temperature, and the solution was further stirred for 18 hours. The completion of the reaction was confirmed by TLC, and thereafter this solution was concentrated under a reduced pressure. The obtained residue was purified by an ion exchange resin (product name: Dowex 50W (registered trademark)×8, maker name: manufactured by The Dow Chemical Company) (H$_2$O→5% NH$_3$), thereby yielding a white solid compound (1b-1) (27.5 mg, 99%).

Compound (1b-1):

$^1$H NMR (500 MHz, D$_2$O): δ=3.89 (dd, J=8.0, 4.0 Hz, 1H), 2.97 (td, J=8.0, 4.0 Hz, 1H), 2.90 (dt, J=10.3, 8.0), 2.56 (td, J=12.0, 5.7 Hz, 1H), 2.52 (td, J=9.7, 5.7 Hz, 1H), 2.38 (td, J=10.3, 5.7 Hz, 1H), 2.29 (td, J=11.5, 4.6 Hz, 1H), 2.22 (q, J=8.6 Hz, 1H), 1.99 (dtd, J=12.0, 9.2, 2.9 Hz, 1H), 1.78-1.55 ppm (m, 7H)

Test Example 1: Electrophysiological Activity in *Xenopus* Oocytes in which Mugineic Acid Iron Complex Transporter HvYS1 was Expressed HvYS1 cDNA (DNA Data Bank of Japan: DDBJ accession No. AB214183) was inserted into the restriction enzyme sites XbaI and BamHI of a pSP64Poly(A) vector (manufactured by Promega), and this vector was used to prepare cRNA by means of a mMESSAGE mMACHINE Kit manufactured by Ambion.

The abdomen of adult female *Xenopus laevis* (purchased from Hamamatsu Seibutsu Kyozai Kabushiki Kaisha) was incised to remove *xenopus* oocytes. The oocytes were transferred to a centrifuge tube in which an OR-2 solution (82.5 mM NaCl, 2 mM KCl, 1 mM MgCl$_2$, 5 mM HEPES (pH 7.6)) containing collagenase type IA (manufactured by Sigma) in a concentration of 2 mg/mL was put, incubated at room temperature for about 2 hours, thereafter washed with the OR-2 solution three times, and further washed with an ND-96 solution (96 mM NaCl, 2 mM KCl, 1 mM MgCl$_2$, 1.8 mM CaCl$_2$, 5 mM HEPES (pH 7.6)) three times. By means of a digital microdispenser (Drummond SCIENTIFIC), cRNA (500 ng/μL, 50 nL) was injected into the *xenopus* oocytes. The oocytes were cultured in the ND-96 solution at 17° C. for 72 hours.

Figure 1:
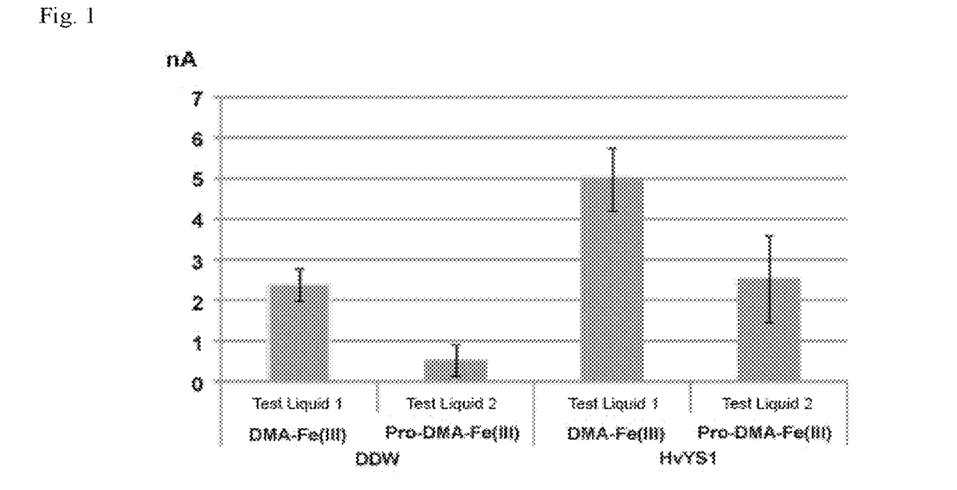
FIG. 1 shows a result of Test Example 1.

Next, an iron complex (test liquid 1) of deoxymugineic acid (DMA) as the substrate of HvYS1 protein and an iron complex (test liquid 2) of the heterocycle-containing amino acid compound (1b-1) (proline-deoxymugineic acid, Pro-DMA) of the present invention were each prepared in the following manner. DMA and Pro-DMA were each dissolved in 10 mM MES/Tris (pH 6.0) buffer so that the concentrations thereof were each 200 mM, and 10 μL of an aqueous solution of 100 mM ferric chloride ($FeCl_3$-$6H_2O$) was mixed with the respective solutions. Further, 113.3 μL of MES/Tris buffer (pH 6.0) was added, and the solutions were stirred at room temperature in a dark room for 2 hours to prepare the respective iron complexes (7.5 mM). The respective iron complexes were subjected to centrifugal filtration (Merk, Ultrafree-MC-GV (UFC30GVNB)) at 14,000 rpm for 15 minutes to form reaction substrates. The oocytes in which HvYS1 was expressed were set in a chamber filled with the ND-96 solution, and 10 μL of the respective prepared substrates (7.5 mM) were applied (final concentration: 50 M) to measure the electrophysiological activity. Two microelectrodes filled with 3 M KCl (internal resistance: 0.5 to 2 MΩ) were inserted into the oocytes, and the potential was fixed, in a mode in which the potential of an experimental tank was fixed to 0 mV, using an Axoclamp-2 type two-electrode potential fixing amplifier (manufactured by Axon). The current was allowed to pass through a 1-kHz low-pass filter (−3 dB, 8-pole Bessel filter/cyber amplifier, manufactured by Axon), sampled at 10 kHz using Degidata 1200 interface (manufactured by Axon), and digitized and stored. ORIGIN 6.1 software (Microcal Software) was used for programming and record of the potential and analysis of the stored data. Measurement was made at a fixed potential of −60 mV. The result is shown in FIG. 1. DDW in FIG. 1 means negative control oocytes into which the same amount of superpure water was injected. The number (n) of measurements is 3 for DDW and 4 for HvYS1.

<Result>

The iron complex of the heterocycle-containing amino acid compound (1b-1) of the present invention [Pro-DMA-Fe(III)] (test liquid 2) was observed to have transporting activity like the deoxymugineic acid iron complex [DMA-Fe(III)] (test liquid 1). From this result, it has been found that Pro-DMA has the ability to transport iron ions into plant bodies like DMA.

It has been reported so far that, when the DMA-iron complex is taken in plant bodies, rice significantly grows even under alkaline conditions (Non-Patent Document 2). Thus, from the result of Test Example 1, it is considered that the metal complex of the heterocycle-containing amino acid compound (1b-1) of the present invention [Pro-DMA-Fe(III)] provides excellent effects as a fertilizer or plant growth regulating agent due to the fact that iron ions are taken in plant bodies.

Test Example 2: Uptake Activity of Isotope Iron Complex in Insect Cells in which Mugineic Acid Iron Complex Transporter HvYS1 was Expressed An insect cell expression system (baculovirus expression/Bac-to-Bac (registered trademark) System) (Invitrogen Life Technologies) was applied to insect cells Sf9 (Invitrogen Life Technologies) to introduce an HvYS1-HIS-tagged gene into a pFast-Bac vector. A bacmid of the HvYS1-HIS-introduced vector and a bacmid of the vector alone were prepared; 2 ml of each of the bacmids was added to 50 ml (2×106 cells) cultured in a medium obtained by adding 4% bovine serum and a penicillin-streptomycin mixed solution (NACALAI TESQUE) to an SF900 II serum-free medium (Invitrogen Life Technologies); and the cells were cultured at 28° C. and 120 rpm for 3 days. The number of the cells in the cell culture solution was counted, and the solution was dispensed into 15-ml centrifugal tubes so that the amount thereof in each of the tubes was 5 ml (2×106 cells).

Next, an isotope iron complex (test liquid 3) of deoxymugineic acid (DMA) and an isotope iron complex (test liquid 4) of the heterocycle-containing amino acid compound (1b-1) (proline-deoxymugineic acid, Pro-DMA) of the present invention were each prepared in the following manner. DMA and Pro-DMA were each dissolved in 10 mM MES/Tris (pH 6.0) buffer so that the concentrations thereof were each 200 mM. One hundred eighty (180) mM ferric chloride ($FeCl_3$-$6H_2O$) and 20.4 mM iron isotope Fe-55 (NEZ043 Lot 031114B 37.0 MBq (PerkinElmer)) (cold 1/5) were each mixed in an amount of 22 μL to prepare iron solutions each having a total concentration of 100 mM. Ten (10) L of DMA/Pro-DMA (200 mM) and 10 μL of iron (100 mM) were mixed with each other; 113.3 μL of MES/Tris Buffer (pH 6.0) was added to the mixtures; the resultant solutions were rotated at room temperature for 2 hours in a dark room to prepare the respective iron complexes (7.5 mM). The respective prepared iron complexes were subjected to centrifugal filtration (Merk, Ultrafree-MC-GV (UFC30GVNB)) at 14,000 rpm for 15 minutes to form reaction substrates.

Figure 2:
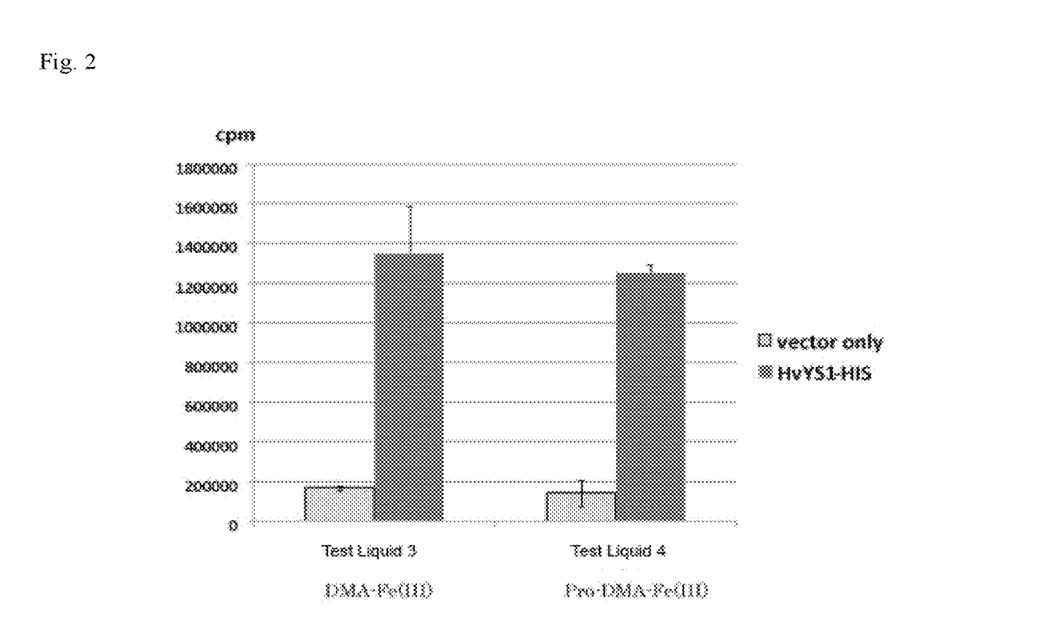
FIG. 2 shows a result of Test Example 2.

Five (5) ml of the Sf9 cell culture solution containing the vector alone and 5 ml of the Sf9 cell culture solution in which HvYS1-HIS was expressed were centrifuged at 1700×g 5 min to collect supernatants; 1 ml of the medium for Sf9 was added to the precipitated cells; the cells were transferred to 2-mL centrifuge tubes; and 7 μL of 7.5 mM Fe(III) complexes were added to the respective tubes (final concentration: 50 μM). The tubes were lightly swung at room temperature for 1 hour to cause the reaction, and supernatants were collected at 1700×g 5 min. After washing with 1.0 ml of PBS three times, PBS was finally removed sufficiently. Three hundred (300) μl of 1 M NaOH and 200 μl of PBS were added to the respective tubes, and dissolved by vortex. To a counting vial (WHEATON No. 986492), 3 ml of a cocktail (ULTIMA GOLD (registered trademark) PerkinElmer) was put, and the whole amount was transferred thereto for counting with a scintillation counter. The result is shown in FIG. 2.

The metal complex of the heterocycle-containing amino acid compound (1b-1) of the present invention [Pro-DMA-Fe(III)] (test liquid 4) was observed to have transporting activity almost similar to that of the deoxymugineic acid metal complex [DMA-Fe(III)] (test liquid 3).

From this result, it has been found that the mugineic acid iron complex transporter 1HvYS1 transports iron complexes of Pro-DMA as well as DMA.

Test Example 3: Growing Test of Rice in Hydroponics

Rice seeds (Nipponbare) were sterilized with 10% hydrogen peroxide solution for 30 minutes, then sufficiently rinsed with distilled water (desalted water), and incubated in distilled water at room temperature overnight. The seeds were seeded on a 96-well plate with the bottom being cut off, and cultivation was started in 250 ml of distilled water. Distilled water was replaced every day, and the seeds were cultivated in a TOMY CFH-415 growth chamber (a photoperiod of 16 h light, 8 h dark at 28° C., a light intensity of 5,700 lux) for one week.

On the other hand, dilution was performed with distilled water so that the respective ingredients indicated in the following Table 1 arrived at the final concentrations indicated therein. The pH was adjusted to 8.0 using 0.5 M $K_2HPO_4$ and 0.5 M $KH_2PO_4$, and the liquids were added to the medium, thereby preparing hydroponic medium test liquids 5 to 8 so that the liquids served as phosphate buffer solutions having a final concentration of 5 mM.

Figure 3:
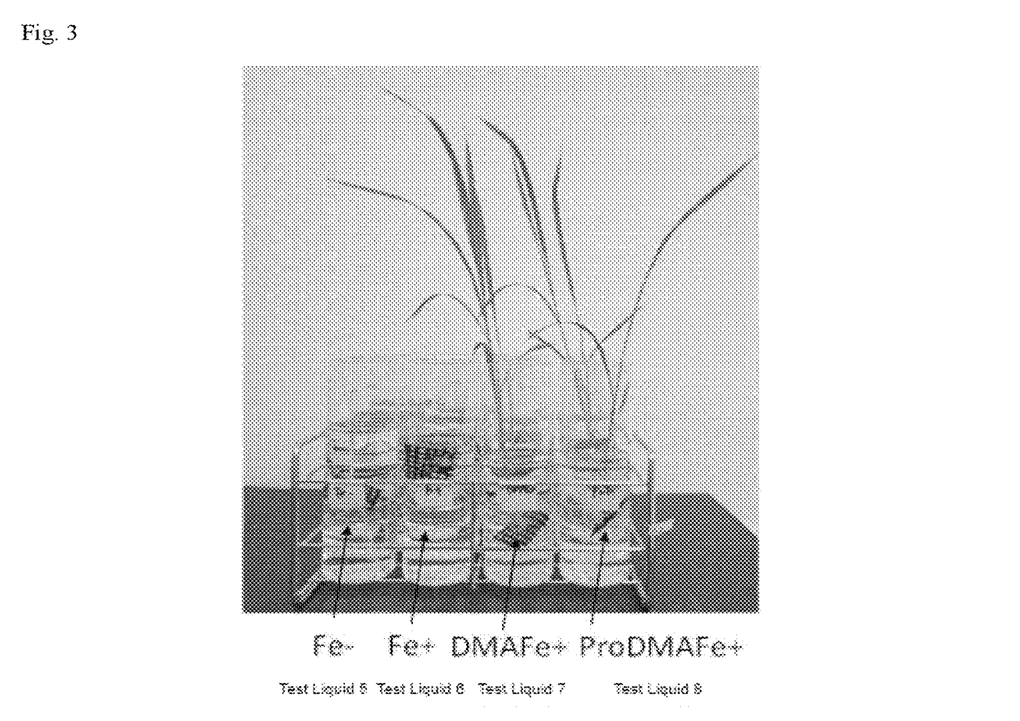
FIG. 3 is a photograph showing a growing state of rice on the third week after seeding in Test Example 3.
Figure 4:
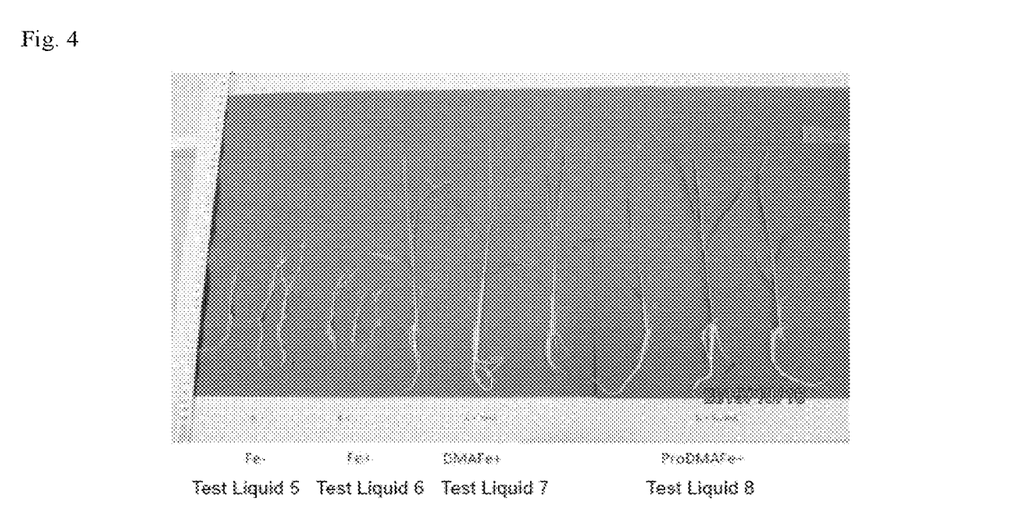
FIG. 4 is a photograph showing growth of rice on the third week after seeding cultivated using each of test liquids in Test Example 3.
Figure 5:
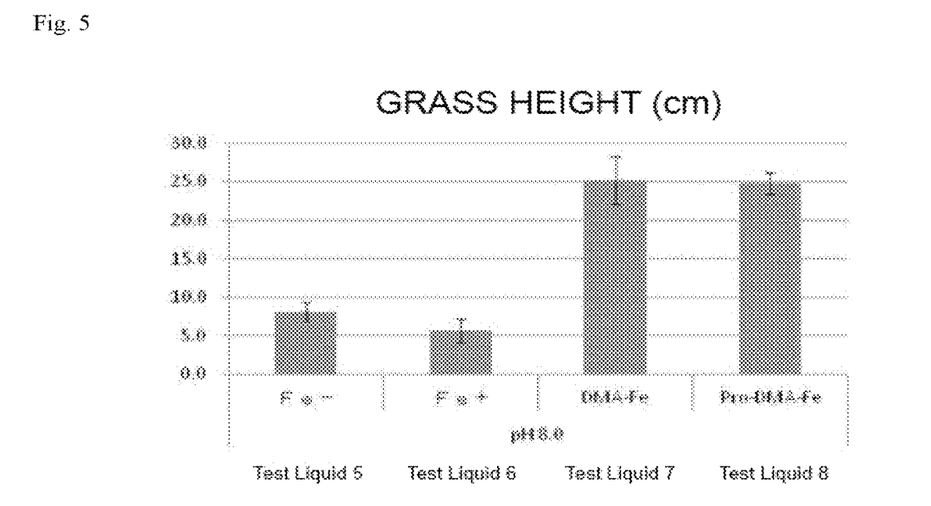
FIG. 5 is a graph showing heights of grasses of rice on the third week after seeding cultivated using each of the test liquids in Test Example 3.
Figure 6:
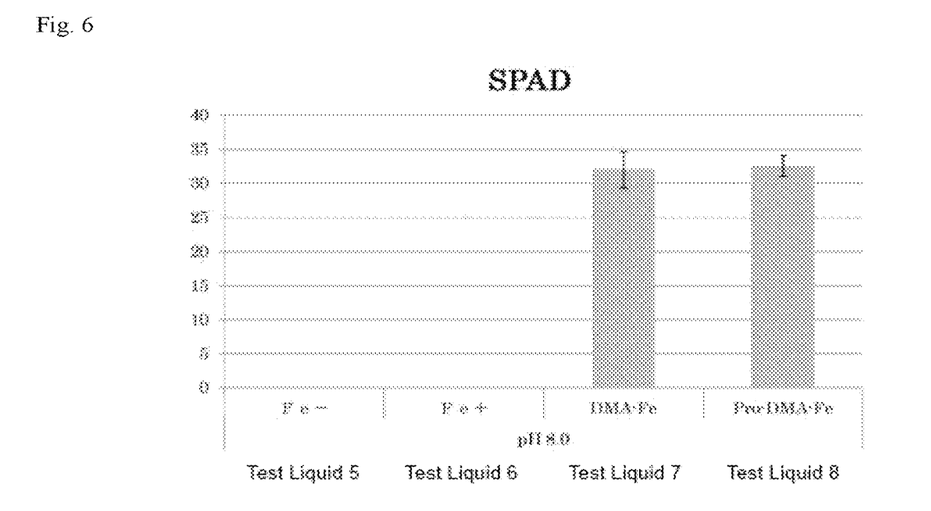
FIG. 6 is a graph showing SPAD values of leaves of rice on the third week after seeding cultivated using each of the test liquids in Test Example 3.

These four types of test liquids were each put, in an amount of 100 ml, in three cultivation tubes to cultivate one seedling of rice in each of the tubes for two weeks. The test liquids were replaced every two or three days. On the third week after seeding, the states of the respective grasses of rice were photographed (FIGS. 3 and 4), and the heights of the rice grasses were measured (FIG. 5). For the leaves of rice on the third week after seeding cultivated using the respective test liquids, the SPAD value (FIG. 6) was measured using SPAD-502 Plus manufactured by KONICA MINOLTA. The SPAD value is a value indicating the content of chlorophyll.

<Result>
As shown in FIGS. 3 to 6, the test liquid 8 containing the compound of the present invention [Pro-DMA-Fe] (ProDMAFe+) provided good growth of rice even in the alkaline medium having a pH of 8.0 at the same level as the test liquid 7 [DMA-Fe] (DMAFe+).

INDUSTRIAL APPLICABILITY

The heterocycle-containing amino acid compound or a salt thereof in the present invention can be used as a fertilizer and a plant growth regulating agent. The compound exerts a great effect on the growth of plants (such as graminaceous plants) also in particularly alkaline soil.

The invention claimed is:

1. A heterocycle-containing amino acid compound represented by the following formula (1):

wherein $R^1$, $R^2$ and $R^3$ are identical with or different from each other, and each represent a hydrogen atom or a carboxyl-protecting group; $R^4$ represents a hydrogen atom or a hydroxyl-protecting group; $R^5$ represents a hydrogen atom or an amino-protecting group; and n represents an integer of 1 or 2, or a salt thereof.

TABLE 1

| | Test Liquid 5 (Fe−) | | Test Liquid 6 (Fe+) | |
|---|---|---|---|---|
| Component | Final concentration (μM) | Component | Final concentration (μM) |
| | | $FeCl_3$•$6H_2O$ | 30 |
| $KNO_3$ | 90 | $KNO_3$ | 90 |
| $Ca(NO_3)_2$•$4H_2O$ | 180 | $Ca(NO_3)_2$•$4H_2O$ | 180 |
| $(NH_4)_2SO_4$ | 180 | $(NH_4)_2SO_4$ | 180 |
| $MgSO_4$•$7H_2O$ | 270 | $MgSO_4$•$7H_2O$ | 270 |
| $KH_2PO_4$ | 90 | $KH_2PO_4$ | 90 |
| $MnCl_2$•$4H_2O$ | 0.5 | $MnCl_2$•$4H_2O$ | 0.5 |
| $(NH_4)Mo_7O_{24}$•$4H_2O$ | 1 | $(NH_4)Mo_7O_{24}$•$4H_2O$ | 1 |
| $ZnSO_4$•$7H_2O$ | 0.4 | $ZnSO_4$•$7H_2O$ | 0.4 |
| $CuSO_4$•$5H_2O$ | 0.2 | $CuSO_4$•$5H_2O$ | 0.2 |
| $H_3BO_3$ | 0.5 | $H_3BO_3$ | 0.5 |

| | Test Liquid 7 [DMA-Fe] (DMAFe+) | | Test Liquid 8 [Pro-DMA-Fe] (ProDMAFe+) | |
|---|---|---|---|---|
| Component | Final concentration (μM) | Component | Final concentration (μM) |
| $FeCl_3$•$6H_2O$ | 30 | $FeCl_3$•$6H_2O$ | 30 |
| DMA | 30 | Compound 1b-1 (Pro-DMA) | 30 |
| $KNO_3$ | 90 | $KNO_3$ | 90 |
| $Ca(NO_3)_2$•$4H_2O$ | 180 | $Ca(NO_3)_2$•$4H_2O$ | 180 |
| $(NH_4)_2SO_4$ | 180 | $(NH_4)_2SO_4$ | 180 |
| $MgSO_4$•$7H_2O$ | 270 | $MgSO_4$•$7H_2O$ | 270 |
| $KH_2PO_4$ | 90 | $KH_2PO_4$ | 90 |
| $MnCl_2$•$4H_2O$ | 0.5 | $MnCl_2$•$4H_2O$ | 0.5 |
| $(NH_4)Mo_7O_{24}$•$4H_2O$ | 1 | $(NH_4)Mo_7O_{24}$•$4H_2O$ | 1 |
| $ZnSO_4$•$7H_2O$ | 0.4 | $ZnSO_4$•$7H_2O$ | 0.4 |
| $CuSO_4$•$5H_2O$ | 0.2 | $CuSO_4$•$5H_2O$ | 0.2 |
| $H_3BO_3$ | 0.5 | $H_3BO_3$ | 0.5 |

2. The compound or salt thereof according to claim 1, wherein the heterocycle-containing amino acid compound represented by the formula (1) is a compound represented by the following formula (1A):

wherein $R^1$, $R^2$, $R^3$, $R^4$, $R^5$ and n are as defined in claim 1.

3. The compound or salt thereof according to claim 1, wherein $R^1$, $R^2$, $R^3$, $R^4$ and $R^5$ are each a hydrogen atom.

4. The compound or salt thereof according to claim 1, wherein n is 1.

5. A complex comprising the compound or salt thereof according to claim 1 and a metal.

6. The complex according to claim 5, wherein the metal is iron.

7. A mixture comprising the compound or salt thereof according to claim 1 and a metal compound.

8. The mixture according to claim 7, wherein the metal compound is an iron compound.

9. A fertilizer or a plant growth regulating agent, comprising the mixture according to claim 7.

10. A fertilizer comprising the compound or salt thereof according to claim 1.

11. A plant growth regulating agent comprising the compound or salt thereof according to claim 1.

* * * * *